US006432729B1

(12) United States Patent
Mundt et al.

(10) Patent No.: US 6,432,729 B1
(45) Date of Patent: Aug. 13, 2002

(54) METHOD FOR CHARACTERIZATION OF MICROELECTRONIC FEATURE QUALITY

(75) Inventors: Randall S. Mundt, Pleasanton; Albert J. Lamm, Hollister, both of CA (US); Mike Whelan, Coppell; Andrew Weeks Kueny, Dallas, both of TX (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 09/408,419

(22) Filed: Sep. 29, 1999

(51) Int. Cl.[7] ............................................. H01L 21/00
(52) U.S. Cl. .............................. 438/8; 438/15; 356/349
(58) Field of Search .......................... 438/8, 9, 14, 15, 438/16; 356/349

(56) References Cited

U.S. PATENT DOCUMENTS

| 5,241,369 A | | 8/1993 | McNeil et al. ............... 356/445 |
| 5,405,488 A | | 4/1995 | Dimitrelis et al. ........... 156/627 |
| 5,525,808 A | * | 6/1996 | Irie et al. ..................... 250/548 |
| 5,703,692 A | | 12/1997 | McNail et al. ............... 356/445 |
| 5,777,729 A | * | 7/1998 | Aiyer et al. .................. 356/237 |
| 5,867,276 A | | 2/1999 | McNail et al. ............... 365/445 |
| 5,889,593 A | * | 3/1999 | Bareket ....................... 356/445 |
| 5,923,423 A | * | 7/1999 | Sawatari et al. ............. 356/349 |
| 6,040,198 A | * | 3/2000 | Komiya et al. ............... 438/16 |
| 6,154,280 A | * | 11/2000 | Borden ........................ 356/376 |

FOREIGN PATENT DOCUMENTS

| EP | 0816926 | 1/1998 |
| WO | WO9945340 | 9/1999 |

OTHER PUBLICATIONS

Bushman, et al. "Scatterometry Measurements For Process Monitoring of Polysilicon Gate Etch", SPIE vol. 32131997, pp. 7–79–90.

* cited by examiner

Primary Examiner—John F. Niebling
Assistant Examiner—Olivia Luk
(74) Attorney, Agent, or Firm—Martine & Penilla, LLP

(57) ABSTRACT

Disclosed is a method for characterizing the quality of microelectronic features using broadband white light. A highly collimated light source illuminates an area of a first wafer using broadband multi-spectral light. The angular distribution of the light scattered from the first wafer is then measured. Generally, the angle of the light source, detector, or both is altered and an angular distribution measurement taken at each angle, producing a scatter signature for the first wafer. Finally, the scatter signature of the first wafer is compared with a known scatter signature of a second wafer of good quality to determine the quality of the first wafer.

7 Claims, 11 Drawing Sheets

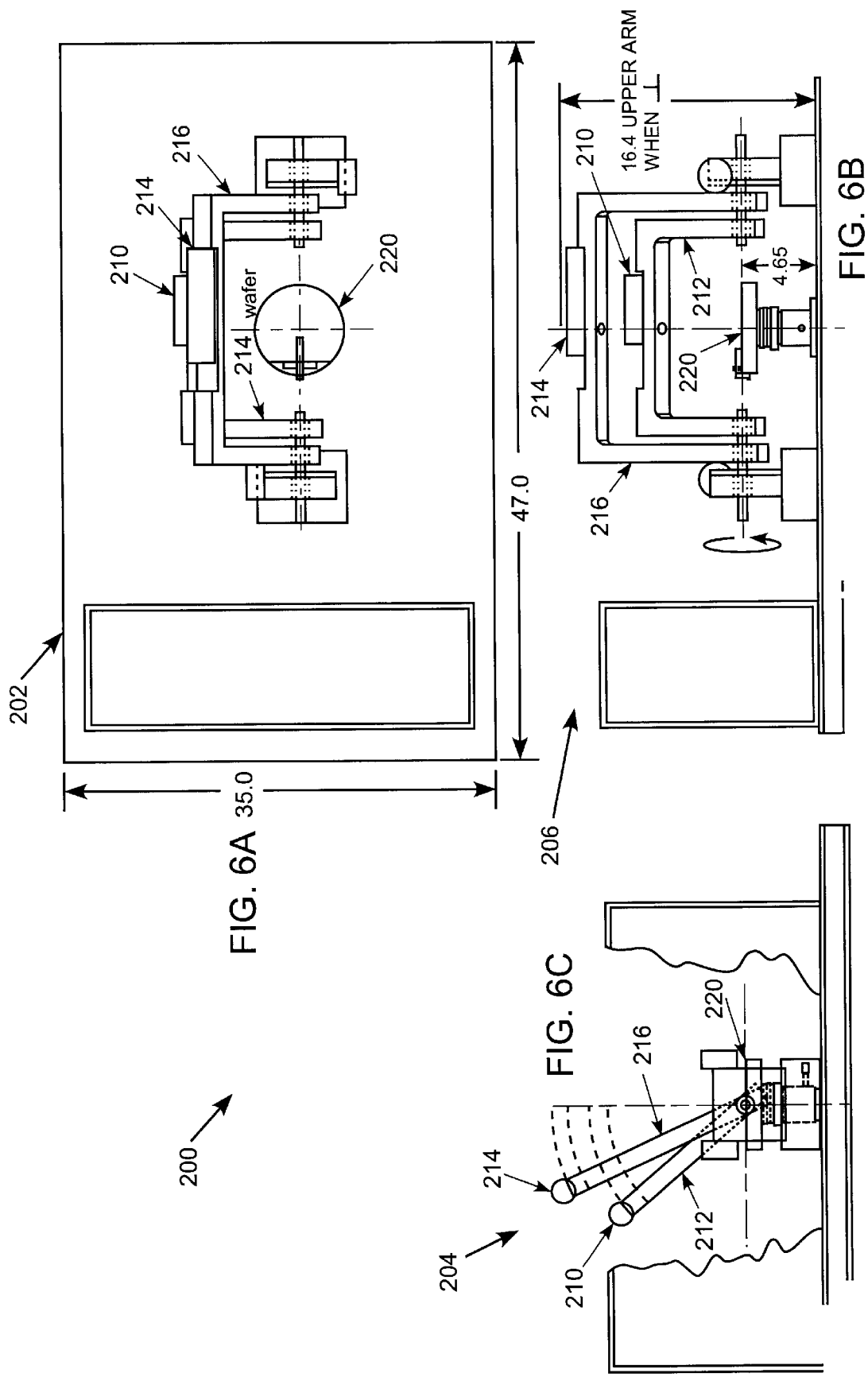

METHOD FOR CHARACTERIZATION OF MICROELECTRONIC FEATURE QUALITY

BACKGROUND OF THE INVENTION

The present invention relates to the fabrication of semiconductor integrated circuits (IC's). More particularly, the present invention relates to methods and apparatuses for the characterization of microelectronic feature quality on IC's.

The fabrication of an integrated circuit requires the various materials comprising the device to be patterned into required circuit elements. This patterning operation is most often accomplished by the deposition of a uniform film layer of a desired material. A "mask" is then formed on the film utilizing a photosensitive material, and finally the exposed material is etched away leaving the desired circuit elements.

The yield and performance of an integrated circuit can be critically dependent upon subtle feature characteristics of the etched circuit elements or features. Some of these important feature characteristics are: line width loss (undercut or "bias"), sidewall angle (slope), surface roughness, the presence of residual material at step edges ("fences" or "stringers"), and the contact angle at the base of the etched feature ("foot"). These etch characteristics result from the complex interaction of the etching chemistry, the plasma physics, and the etch system design and maintenance.

The function of semiconductor equipment manufacturers is to develop hardware, processes, and control systems capable of reliably and reproducibly creating the specific set of conditions required to produce the desired etched feature characteristics. The ability to develop and optimize the etch process and hardware is critically dependent upon the availability of sensors and instruments capable of measuring these important characteristics. What can not be measured, can not be optimized or reliably reproduced.

Furthermore, the time delay between when the etch takes place and when the etch characteristics are measured is of great importance. Measurements that are made while the etch is being performed (e.g., etch rate via endpoint detection) are generally used to provide immediate process feedback, and thus maintain optimal results. Measurements that are performed immediately after the etch process, are typically used for fault detection and to provide "run-to-run" compensation for process drift or hardware aging. Measurements which require significant time delays or human interaction and interpretation are generally used for basic process and hardware development but are not, in general, useful for optimizing and maintaining the process.

Many of the subtle but critical etch characteristics (e.g., sidewall angle, stringer formation, residue, etc.) can presently only be monitored through the use of Scanning Electron Microscopy (SEM) or other complex instrumentation. These techniques are time consuming, very localized, frequently damaging to the wafer, and require substantial human evaluation and interpretation. As such, SEM characterization is intensively used during process and hardware development, but is of limited use in maintaining a process at its optimum condition. SEM's main application in integrated circuit manufacturing is in the detailed analysis and evaluation of problems detected via some other means, such as yield decreases. Since subtle changes in the etch characteristics, which typically result in yield loss, are generally not actively monitored, substantial numbers of wafers are placed at risk.

Another technique for analyzing wafer quality is Scatterometry. Scatterometry is based upon the analysis of light reflected or scattered from the surface of a wafer being evaluated. Scatterometry based sensors are presently available which can measure average surface roughness, estimate feature profile, and determine feature spacing, periodicity, and height. These sensors typically utilize monochromatic laser light reflected from specially designed periodic, diffraction grating like structures to monitor the characteristics of the features. The requirement for a special test structure on the wafer severely limits and complicates the use of these instruments for process control and/or real time fault detection. Moreover, different and specific configurations are required for the measurement of different feature attributes.

In view of the above, what is needed are methods and systems for providing an indication of wafer quality that are not time consuming, damaging to the wafer, or that require substantial human evaluation and interpretation. In addition, the methods should not require special test structures on the wafer, and should be economically viable.

SUMMARY OF INVENTION

The present invention addresses these needs by providing a system and method for characterizing the quality of microelectronic features utilizing broadband white light. In one embodiment, a highly collimated light source illuminates an area of a first wafer using multi-spectral light. Preferably, the highly collimated light source has an angular spread of less than ±1°, and more preferably, less than ±0.5°. The angular distribution of the light scattered from the first wafer is then measured. Generally, the angle of the light source, detector, or both is altered and an angular distribution measurement taken at each angle, producing a scatter signature for the first wafer. Finally, the scatter signature of the first wafer is compared with a known scatter signature of a second wafer of good quality to determine the quality of the first wafer.

In another embodiment, an apparatus for characterizing the quality of microelectronic features utilizing broadband white light is disclosed. The apparatus includes a broadband collimated light source, which is suitable for illuminating a surface of a first wafer with a light beam. The apparatus further includes a light detector, which is suitable for sensing light scattered from the illuminated surface of the first wafer. Finally, a computer for comparing a scatter signature of the first wafer with a known scatter signature of a second wafer of good quality is included.

In yet another embodiment of the present invention, a method for making an integrated circuit structure having monitored feature characteristics is disclosed. The method begins by illuminating an area of a first wafer using a highly collimated light source, wherein the light source produces broadband multi-spectral light. Preferably, the highly collimated light source has an angular spread of less than ±1°, and more preferably, less than ±0.5°. The angular distribution of the light scattered from the first wafer is then measured. Generally, the angle of the light source, detector, or both is altered and an angular distribution measurement taken at each angle, producing a scatter signature for the first wafer. The scatter signature of the first wafer is then compared with a known scatter signature of a second wafer of good quality to determine the quality of the first wafer. Finally, the wafer is processed through a series of semiconductor processes to form the integrated circuit.

Advantageously, the present invention provides an indication of the wafer quality in a timely manner. In addition, the present invention does not require substantial human evaluation and interpretation since the scatter signatures may be readily analyzed on a computer system. Finally, since the present invention provides wafer quality data without the need of complex equipment, the cost of the system remains relatively low.

BRIEF DESCRIPTION OF THE DRAWINGS

The invention, together with further advantages thereof, may best be understood by reference to the following description taken in conjunction with the accompanying drawings in which:

FIGS. 6A, 6B, and 6C are respective plan, elevational, and elevational views showing a system for characterizing the quality of microelectronic features using broadband white light, in accordance with one embodiment of the present invention;

DETAILED DESCRIPTION OF THE INVENTION

An invention is disclosed for characterizing the quality of microelectronic features using angularly resolved broadband white light. In the following description, numerous specific details are set forth in order to provide a thorough understanding of the present invention. It will be apparent, however, to one skilled in the art, that the present invention may be practiced without some or all of these specific details. In other instances, well known process steps have not been described in detail in order not to unnecessarily obscure the present invention.

Figure 1:
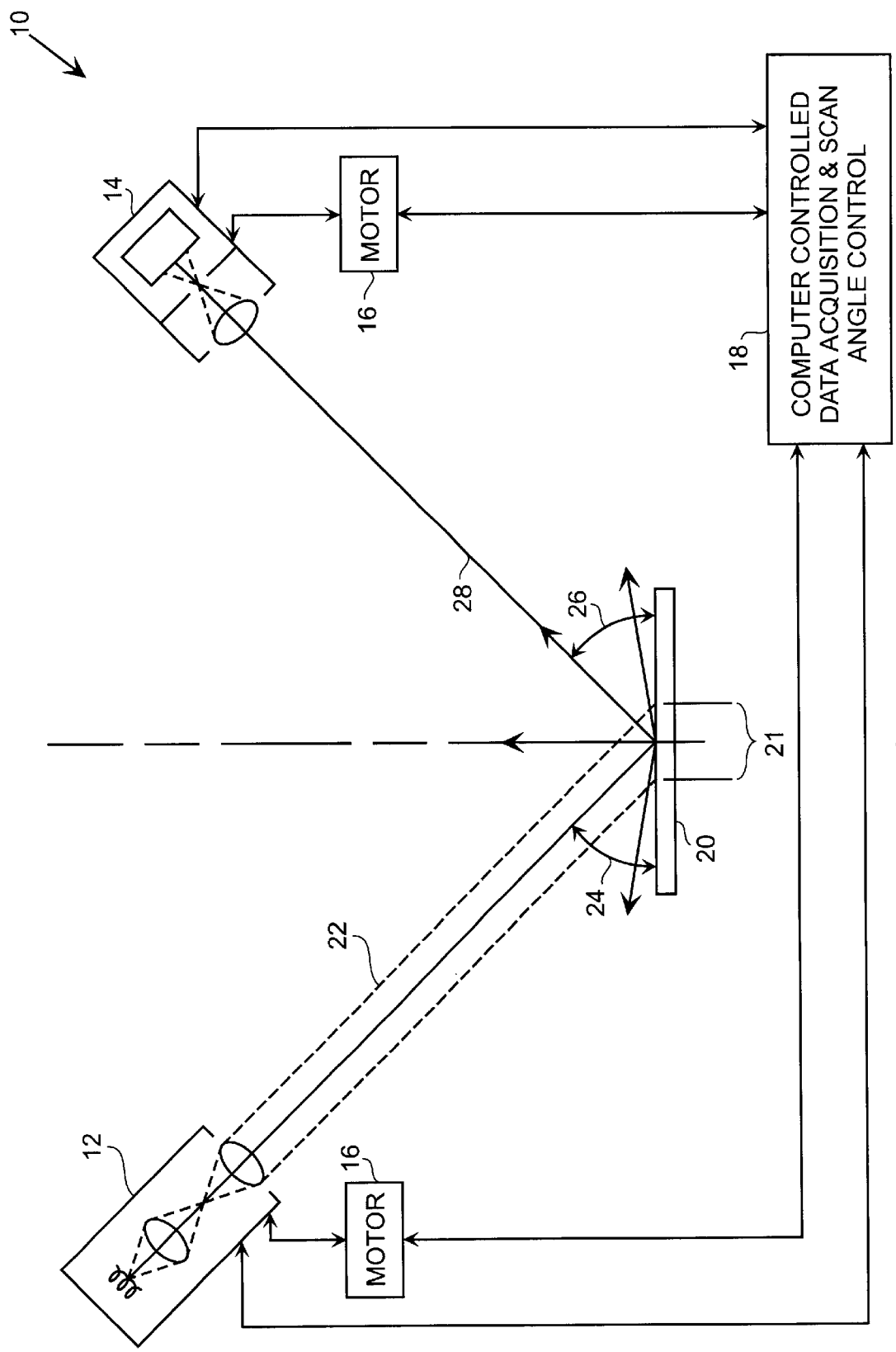
FIG. 1 is an illustration showing a system for characterizing the quality of microelectronic features using broadband white light, in accordance with an embodiment of the present invention.

FIG. 1 is an illustration showing a system 10 for characterizing the quality of microelectronic features using broadband white light, in accordance with one embodiment of the present invention. The system 10 includes a light source 12, a light detector 14, motors 16, and a computer controlled data acquisition and scan angle control 18. Preferably, the light source 12 is well collimated so as to produce a narrow range of incident angles, as described in detail subsequently.

In use, the collimated light source 12 illuminates an area 21 of a wafer 20 with a light beam 22. Preferably, the light beam 22 produced by the light source 12 is spectrally broad. As described before, conventional scatterometry measurements are generally performed using monochromatic light, typically from a laser. The present invention preferably uses a spectrally broadband light source, within a range of about 200 nm to 900 nm, to make the coherence length of the incident illumination short. In this manner, spatial information on the wafer, which corresponds to large-scale structures (such as details of the circuit pattern), is suppressed in the scattering profile.

Next, the light detector 14 is used to measure the intensity of light scattered from the surface of the wafer 20. In one embodiment, motors 16 are used to sweep the incident angle 24 and scattering angle 26 about the wafer 20. By moving the light source 12, the incident angle 24 between the light beam 22 and the surface of the wafer 20 can be changed. Similarly, by moving the light detector 14, the scattering angle 26 between the scattering light beam 28 and the surface of the wafer 20 can be changed.

The motors 16 are controlled by the computer controlled data acquisition and scan angle control 18. In addition, the computer controlled data acquisition and scan angle control 18 is used to analyze light intensity data, which is gathered from the scattering light by the light detector 14.

As stated above, the light beam is 22 is preferably well collimated to ensure the scattering angle 26 from one side of the illuminated area 21 is essentially the same as the scattering angle 26 from the other side of the illuminated area 21. Preferably, the highly collimated light source 12 has an angular spread of less than ±1°, and more preferably, less than ±0.5°. The rays of the light beam 22 are preferably parallel as they travel from the light source 21 to the illuminated area 21 in order to illuminate every feature of the wafer the same. Similarly, the rays of scattered light 28 which will be detected are preferably parallel as they travel from the illuminated area 21 to the light detector 14 in order to measure light at a single angle from each feature. The result is a measurement of the distribution of how each feature interacts with the light.

In addition, the light beam produced by light source 12 is preferably spectrally broad. As described previously, conventional scatterometry measurements are generally performed using monochromatic light, typically from a laser. The present invention preferably uses a spectrally broadband light source to ensure the coherence length of the incident illumination is short. In this manner, spatial information on the wafer, which corresponds to large-scale structure (such as details of the circuit pattern), is suppressed in the scatter signature.

Furthermore, the illumination area 21 is preferably large in order to render the light intensity measurements insensitive to relative die position within the wafer 20. In addition, a large spot size greatly simplifies the practical and cost effective integration of the present invention as a production tool. Small illumination areas 21 result in the scattered light becoming very sensitive to which particular features are illuminated in a particular illumination area 21. In addition, changes in the feature sizes are not averaged out.

It is desirable to have a reasonable degree of spatial averaging on the wafer 20. Thus, the illumination area 21 is preferably on the order of the average die size present on the wafer 20. In this manner, the features within the illumination area 21 do not change as the illumination area 21 is moved over the wafer 20. Preferably, the illumination area 21 is no less than 50% of a repeating unit size on the wafer.

In addition, it is desirable to average in the scribe lines between the dies on the wafer 20, otherwise the process is sensitive to the exact placement of the illumination area 21. If the illumination area 21 were required to be placed within a die area without encompassing any scribe lines, the process would be limited for use only with dies of a predetermined size. In such a process, any smaller die would incorporate scribe lines, and therefore, since the scribe lines are not averaged in, would corrupt the measurement. Thus, the scribe lines are preferably averaged in using the present invention.

To accomplish this, about one half of the illumination area 21 is generally placed on a first die, while the other portion of the illumination area 21 is placed on a second die. In this manner a scribe line is included in the measurement, which is a relatively small portion of the overall scatter signal recorded by the light detector. In addition, using a large illumination area 21 results in the ratio of the portion of the scatter signal that is scribe line, to the portion of the scatter signal that is actual circuit, remaining constant throughout the measuring process. Thus, the use of a large illumination area 21 reduces the accuracy needed in positioning the illumination area 21 relative to a die on the wafer, and therefore reduces or eliminates the need for costly image recognition systems for illumination positioning.

Figure 2:
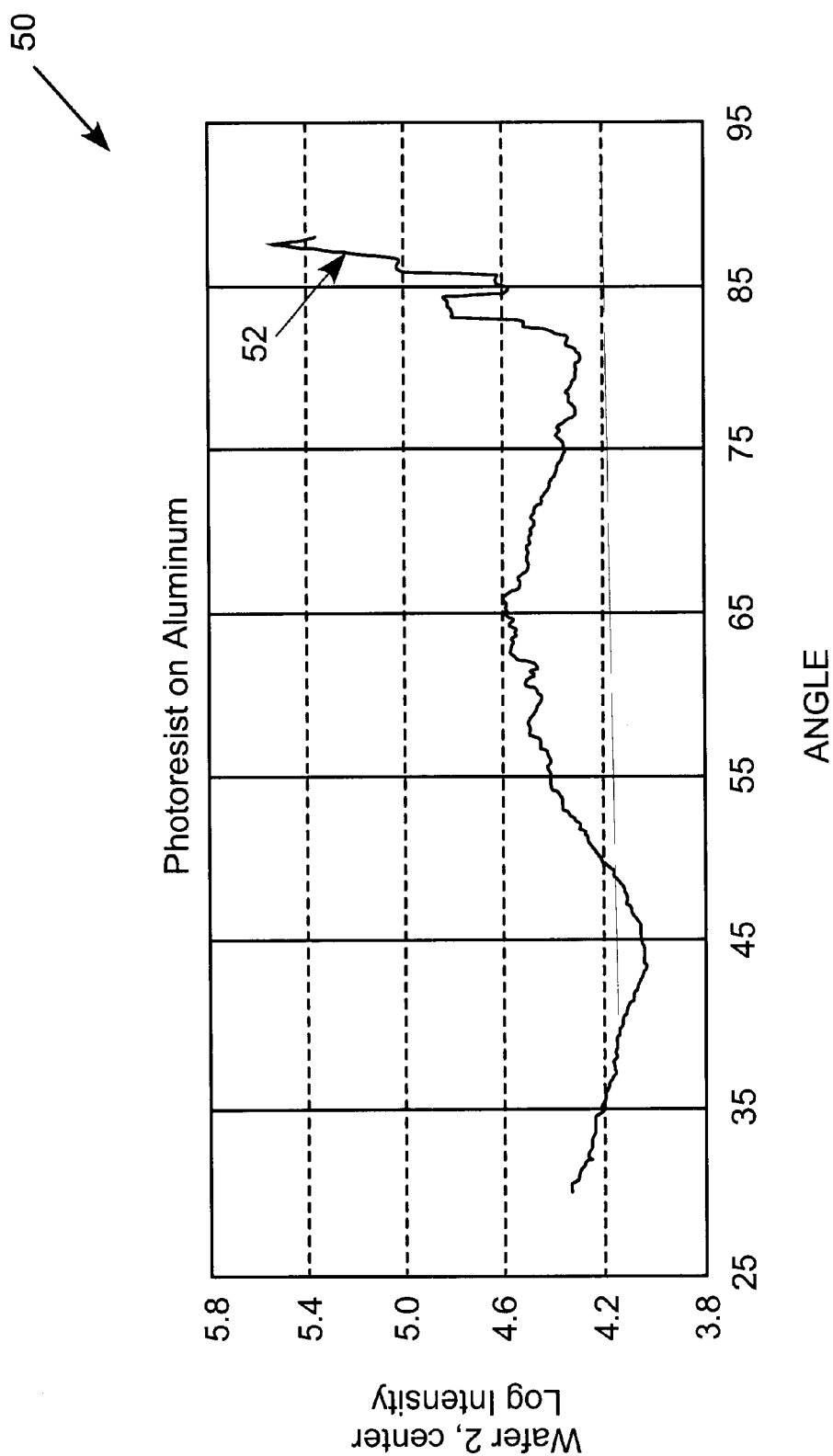
FIG. 2 is a graph of a scatter signature of light scattered from the surface of a wafer, in accordance with another embodiment of the present invention.

Turning next to FIG. 2, a graph 50 of a scatter signature 52 of light scattered from the surface of a wafer is shown, in accordance with another embodiment of the present invention. The scatter signature 52 is the amplitude of the scattered light as a function of the scattering angle. The intensity shown is the log of the intensity of light scattered from the surface of the wafer. Furthermore, a scattering angle of 0° is parallel to the surface of the wafer, while a scattering angle of 90° is normal to the surface of the wafer. In addition, the scatter signature 52 of FIG. 2 was created by keeping the incident angle fixed at about 90° while varying the scattering angle.

Preferably, the scatter signature 52 is first created for a known sample wafer of good quality. The quality of the known sample wafer should be independently verified by some independent verification means, such as SEM. Thereafter, the scatter signatures of future wafers may be compared to the scatter signature 52 of the known sample wafer.

Figure 3:
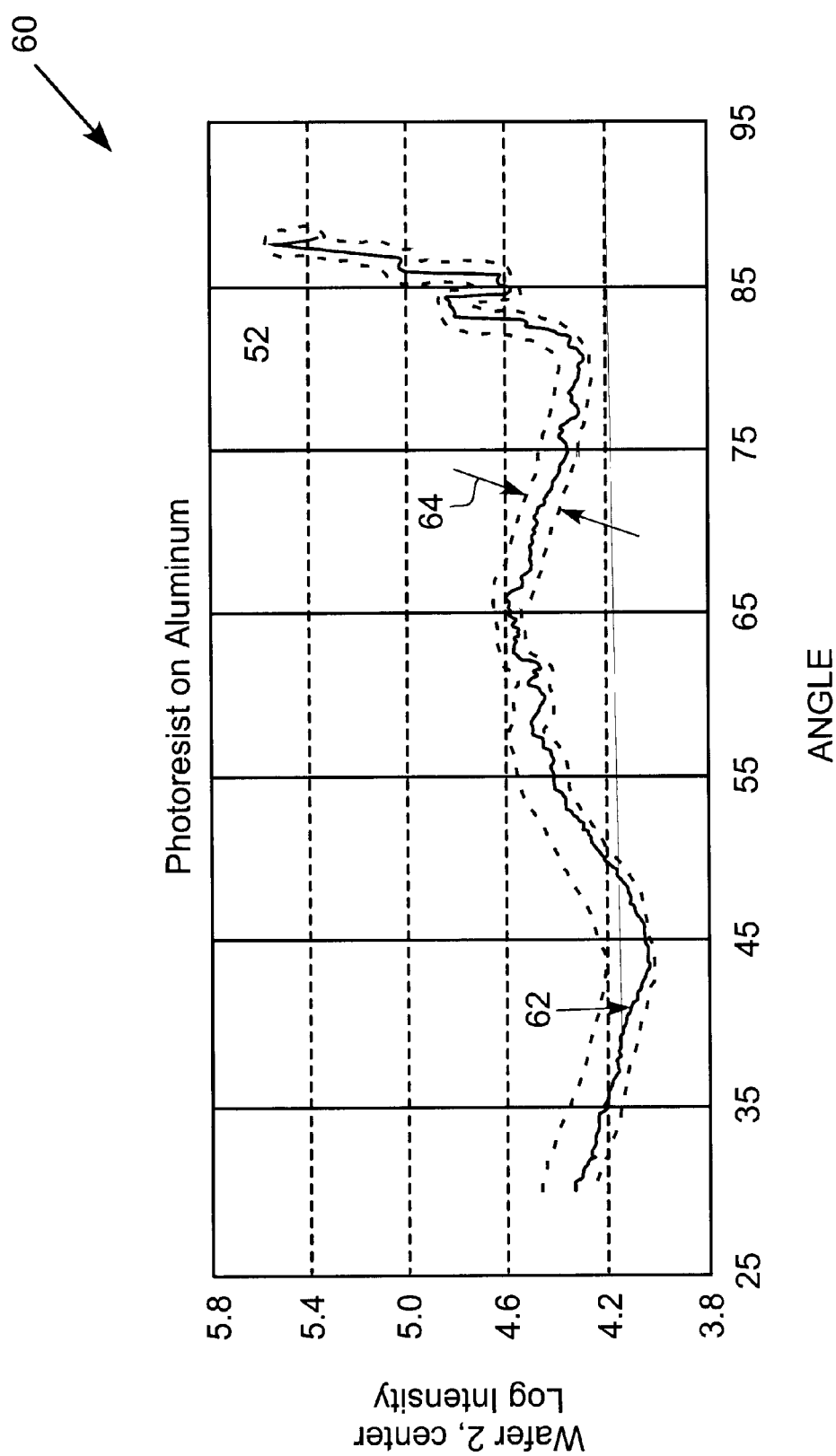
FIG. 3 is a graph of a scatter signature with related quality bounds, in accordance with yet another embodiment of the present invention.

FIG. 3 is a graph 60 of a scatter signature 62 with related quality bounds 64, in accordance with another embodiment of the present invention. The bounds 64 may be statistically established by observing variations in known acceptable wafer samples. The result is a set of quality bounds 64, above and below, the scatter signature 62 of the known sample wafer of good quality.

Thereafter, scatter signatures of future wafers may be compared to the scatter signature 62 of the known sample wafer. If a future wafer's scatter signature falls within the quality bounds 64, there is a good indication that the wafer is of good quality. In addition, using a broadband light source, as in the present invention, makes it much easier to interpret the scattered light data.

Figure 4:
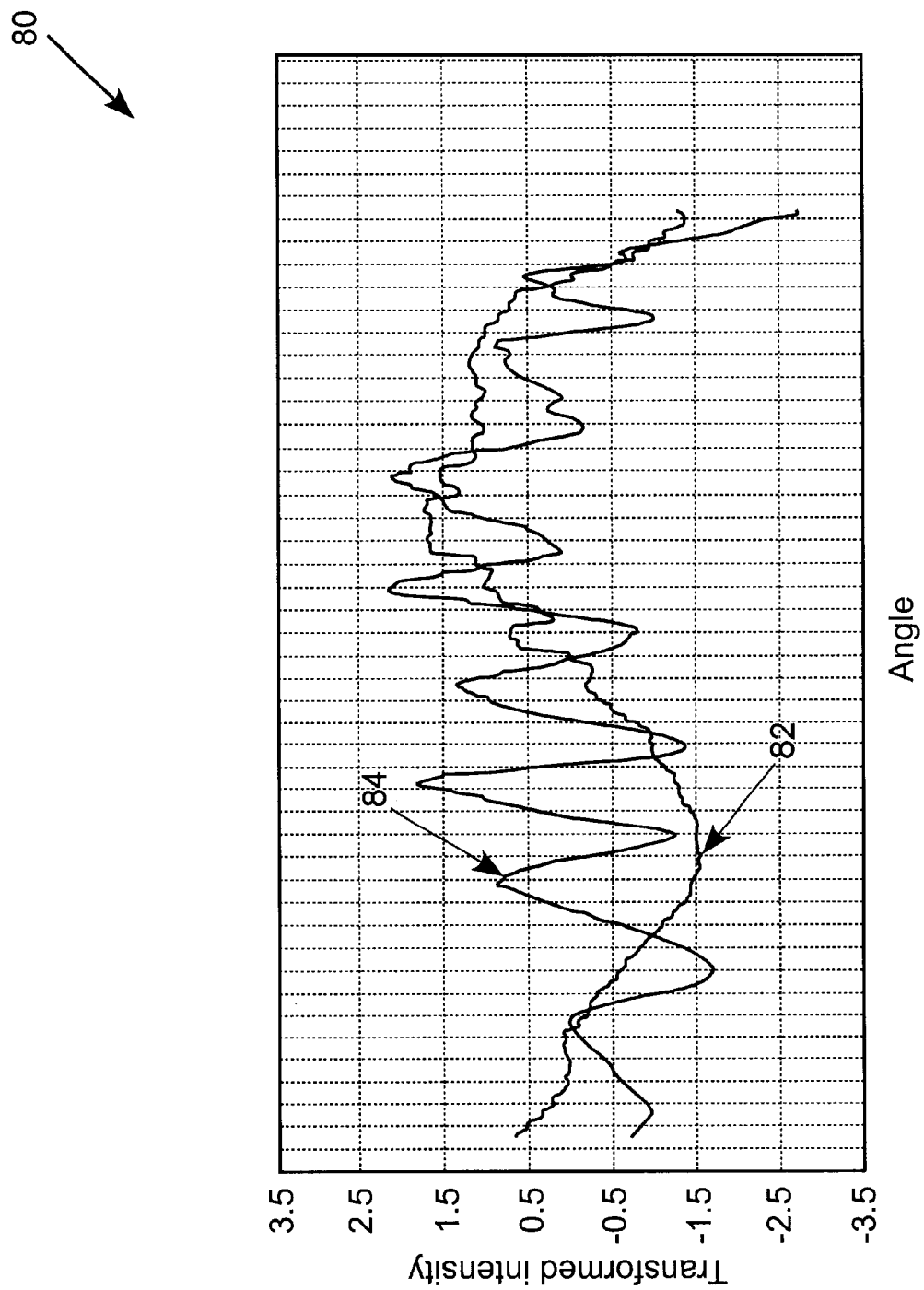
FIG. 4 is a graph showing the scatter signature of a "white" light source and a monochromatic light source, in accordance with an embodiment of the present invention.

FIG. 4 is a graph 80 showing the scatter signature of a "white" light source 82 and a monochromatic light source 84. The scatter signature of the "white" light source 82 and the monochromatic light source 84 is the amplitude of the scattered light as a function of the scattering angle. The intensity shown is the log of the intensity of light scattered from the surface of the wafer. In addition, a scattering angle of 0° is parallel to the surface of the wafer, while a scattering angle of 90° is normal to the surface of the wafer.

As the graph 80 shows the scatter signature of the monochromatic light source 84 includes wide swings caused by diffraction effects from diffraction of the top and bottom of features located on the wafer. Since the top and bottom of the features (i.e., the etch depth) is known by how thick a film is deposited, the etch depth is not an important characteristic of the etch quality measurement. The use of monochromatic light results in very large signal oscillations imposed upon the background signal caused by the features on the wafer. These signal oscillations make the interpretation of the scatter data and the determination of whether the signature falls within the quality bounds very difficult. Therefore, the present invention uses broadband incident light to suppress the spatial information caused by large-scale features on the wafer.

It should be borne in mind that the present invention gathers measurements on actual product wafers. Conventional scatterometry uses special test wafers and patterns so as to simplify the interpretation of the measurement in terms of analytical diffraction models. The complexity of the patterns on "real" integrated circuits renders this approach impractical. In the present invention, classical diffraction effects are intentionally suppressed by integrating over a large area using broadband illumination. A central component of this invention is the discovery that measurements made in accordance with the disclosed method and apparatus are sufficiently sensitive and reproducible so as to reveal changes in etch characteristics of practical importance.

Figure 5A:
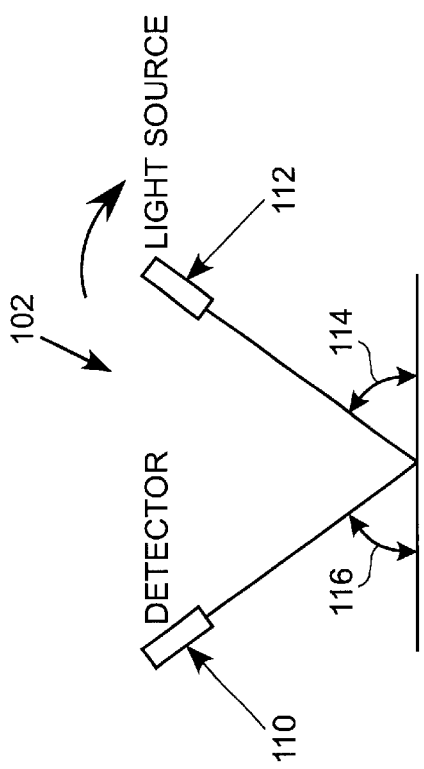
FIG. 5A is an illustration showing a fixed light configuration, in accordance with one aspect of the present invention.

Referring next to FIGS. 5A–5D, illustrations are presented showing various configurations of the present invention. FIG. 5A is an illustration showing a fixed light configuration 100, in accordance with one aspect of the present invention. The fixed light configuration 100 includes a light detector 110 and a light source 112. In the fixed light configuration 100, the light source 112 is fixed at a constant incident angle 114 throughout the detection process. The light detector 110 is then swept though a series of scatter angles 116 to capture the scattered light data. Preferably, the detector is swept from about −70° to +70°, one scattered light measurement being made for each scatter angle 116.

Figure 5B:
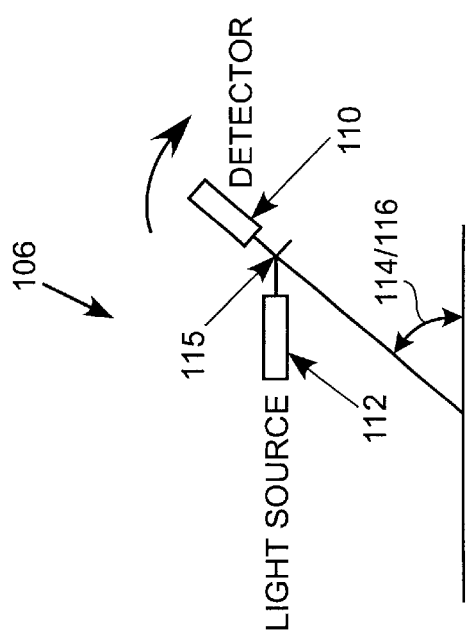
FIG. 5B is an illustration showing a fixed detector configuration, in accordance with another aspect of the present invention.

FIG. 5B is an illustration showing a fixed detector configuration 102, in accordance with another aspect of the present invention. The fixed detector configuration 102 includes a light detector 110 and a light source 112. In the fixed detector configuration 102, the light detector 110 is fixed at a constant scatter angle 116 throughout the detection process. The light source 112 is then swept through a series of incident angles 114 to vary the incident angle. Preferably, the light source is swept from about 70° to near 0° (normal to the surface of the wafer), one scattered light measurement being made for each incident angle 114.

Figure 5C:
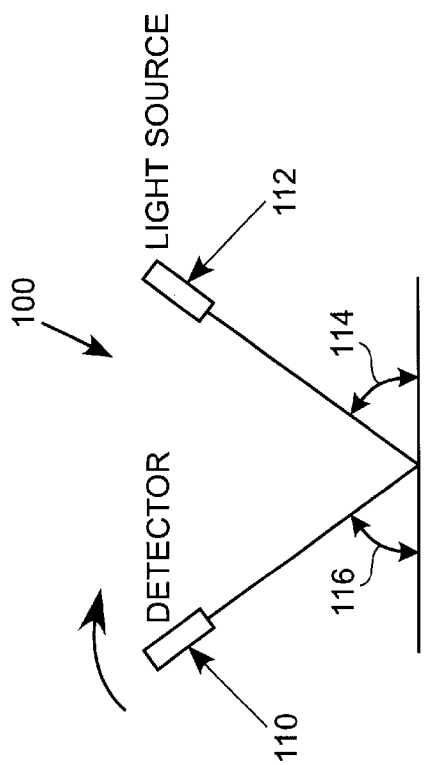
FIG. 5C is an illustration showing a variable configuration, in accordance with another aspect of the present invention.

FIG. 5C is an illustration showing a variable configuration 104, in accordance with another aspect of the present invention. The variable configuration 104 includes a light detector 110 and a light source 112. In the variable configuration 104, both the light detector 110 and the light source 112 are swept though a series of angles, varying both the incident angle 114 and the scatter angle 116. Preferably, both the light source and the detector are swept from about 0° normal to the surface to 70°, one scattered light measurement being made for each scatter angle 116. In another embodiment, one scattered light measurement is made for each incident angle 114 as well each scatter angle 116. In yet another embodiment, one scattered light measurement is made for each incident angle 114 only. The offset angle 118 between the incident angle 114 and scatter angle 116 may be varied.

Figure 5D:
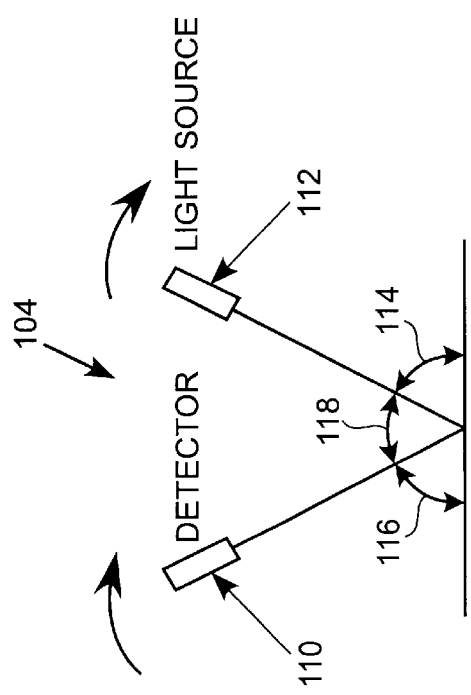
FIG. 5D is an illustration showing a fixed-variable configuration, in accordance with another aspect of the present invention.

FIG. 5D is an illustration showing a fixed-variable configuration 106, in accordance with another aspect of the present invention. The fixed-variable configuration 106 includes a light detector 110, a light source 112, and a beam splitter 115. In the fixed-variable configuration 106, both the light detector 110 and the light source 112 are swept though a series of angles, varying both the incident angle 114 and the scatter angle 116. Preferably, both the light source and the detector are swept from about −70° to +70°, one scattered light measurement being made for each incident angle 116. However, unlike the variable configuration 104, the offset angle between the incident angle 114 and scatter angle 116 is kept constant at a 0°.

FIGS. 6A, 6B, and 6C are diagrams showing system 200 for characterizing the quality of microelectronic features using broadband white light, in accordance with one embodiment of the present invention. The showing of system 200 includes a top view 202 (FIG. 6A), a side view 204 (FIG. 6B), and a front view 206 (FIG. 6C). The system 200 includes a well collimated light source 210 attached to a source arm 212, and a light detector 214 attached to a detector arm 216. Furthermore, both the source arm 212 and the detector arm 216 are movable about a wafer 220.

In use, the source arm 212 is used to move the light source 210 about the wafer 220. Similarly, the detector arm 216 is used to move the light detector 214 about the wafer 220. Advantageously, the system 200 is capable of moving the light source 210 about the surface of the wafer 220, while keeping the light detector 214 at a fixed angle to the surface of the wafer 220, and vice versa. Furthermore, the system 200 is capable of moving both the light source 210 and the light detector 214 simultaneously about the surface of the wafer 220, either at a fixed offset angle or a variable offset angle. Thus, the apparatus of FIGS. 6A, 6B, and 6C provides a great degree of freedom in measuring scattered light from the surface of the wafer 220.

Figure 7:
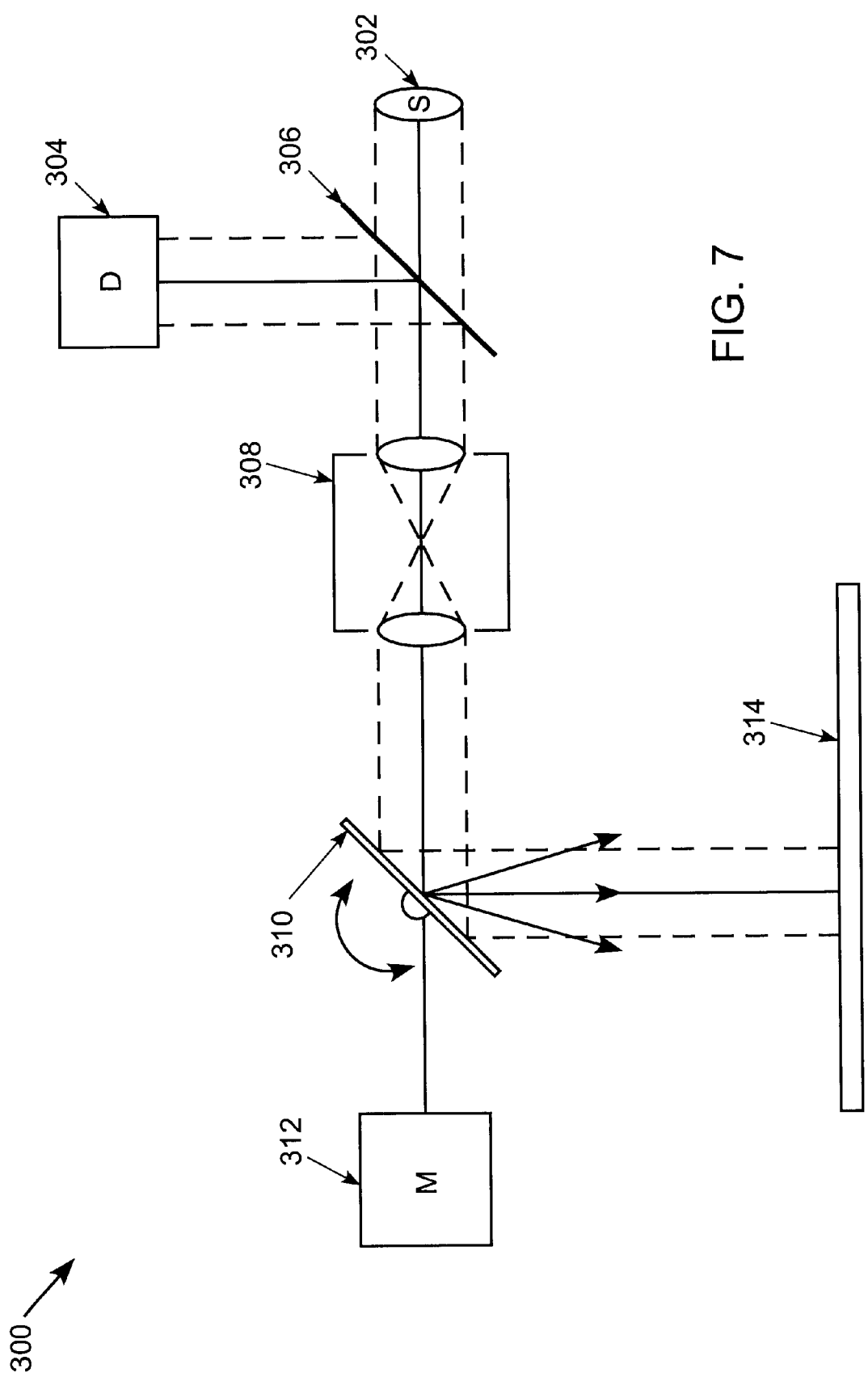
FIG. 7 is an illustration showing a coaxial configuration, in accordance with another embodiment of the present invention.

Referring next to FIG. 7, a coaxial configuration 300 is shown, in accordance with an embodiment of the present invention. The coaxial configuration 300 includes a light source 302, a light detector 304, a beam splitter 306, a collimator 308, a rotatable mirror 310, and a motor 312 attached to the rotatable mirror 310. The coaxial configuration 300 is used to gather scatter data from the surface of a wafer 314 without the need to move the actual light source 302 or the light detector 304.

In operation, light travels from the light source 302 through the beam splitter 306 to the collimator 308, which collimates the light. The collimated light then travels to the rotatable mirror 310, which reflects the light to and from the surface of the wafer 314. The rotatable mirror 310 is capable of being rotated about an axis utilizing the motor 312. Since the rotatable mirror 310 is capable of rotating about an axis, the mirror 310 is used to direct the light beam across the surface of the wafer 314. In this manner, the light source 302 and the light detector 304 may remain stationary while still being able to gather scattered light data at varying incident angles and scattering angles. This is desirable since the light source 302 and light detector 304 have power supplies, cooling requirements, and other systems that would increase the complexity of the system if they are required to be movable.

In addition, the coaxial configuration 300 allows the use of one collimator 308. Both the light beam and the scatter signal travel over the same optics, using the same optics twice. First as a beam former for the light traveling to the wafer 314, and second as a telescopic optic for the scatter signal traveling from the wafer 314 to the light detector 304. In this manner, the two divergences are automatically matched.

In addition, to achieve a higher signal-to-noise ratio and cancel out dark currents and other noise, the light is preferably chopped at a particular frequency. The detection is then synchronized to that frequency to make use of the equivalent of a phase-locked loop.

Figure 8:
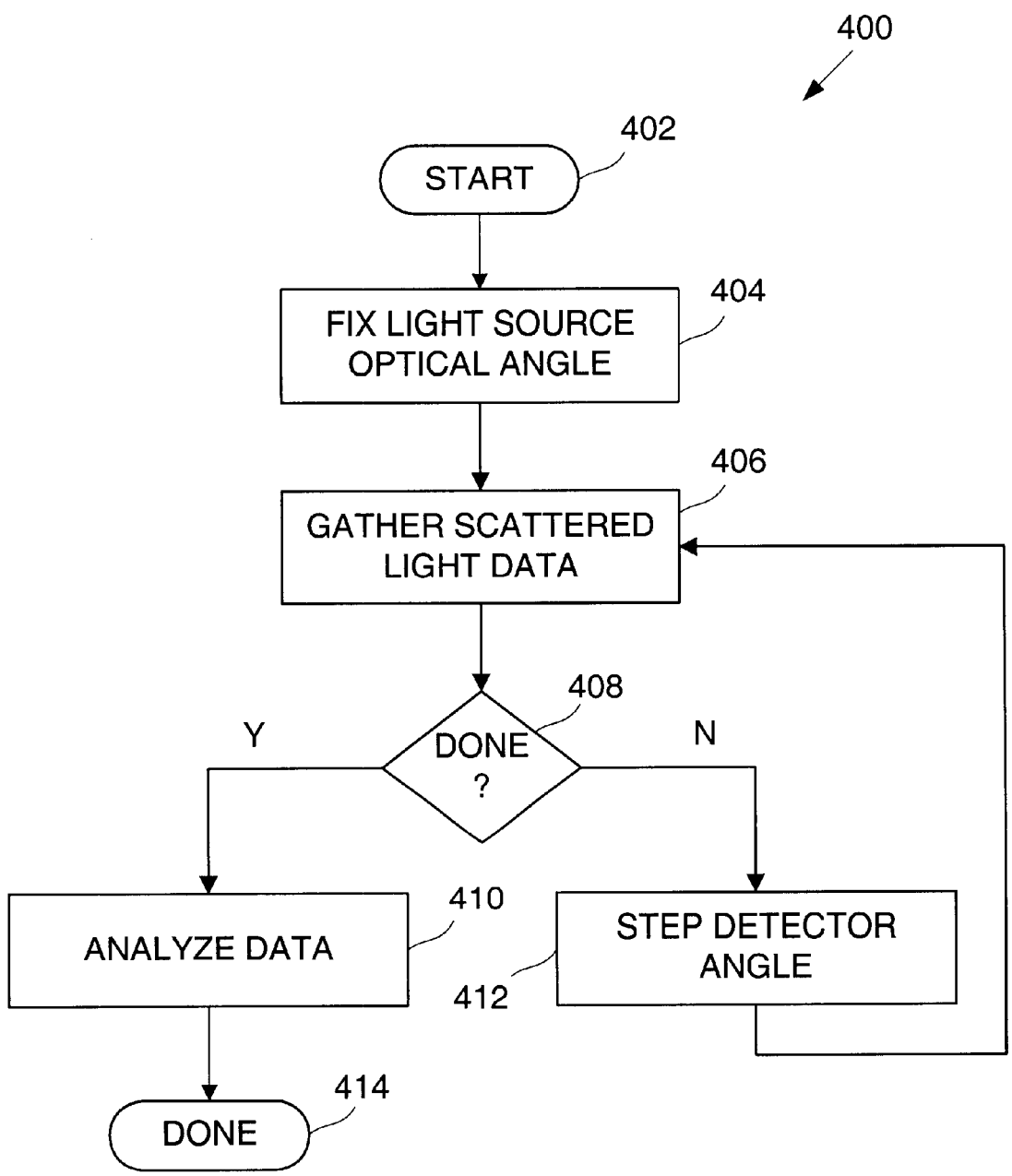
FIG. 8 is a flowchart showing a method for monitoring the feature characteristics of etched wafers, in accordance with an embodiment of the present invention.

FIG. 8 is a flowchart showing a method 400 for monitoring the feature characteristics of etched wafers, in accordance with an embodiment of the present invention. In an initial operation 402, preprocess operation are performed. Preprocess operations include preparing a wafer for etching, and etching the wafer.

In a fixed angle operation 404, a well collimated light source optical angle is fixed. The collimated light source optical angle is fixed at a predetermined angle with the wafer surface. The light source is then used to illuminate an area on the surface of the wafer. As discussed above, the light source may directly illuminate the wafer surface, or indirectly illuminate the wafer surface using a mirror.

In addition, the light beam produced by light source is preferably spectrally broad. As described before, conventional scatterometery measures are generally performed using monochromatic light, typically from a laser. The present invention preferably uses a spectrally broadband light source to make the coherence length of the incident illumination short. In this manner, spatial information on the wafer, which corresponds to large-scale structures (such as details of the circuit pattern), is suppressed in the scatter signature.

Furthermore, the illumination area is preferably large to render the light intensity measurements insensitive to relative die position within the wafer. In addition, a large spot size greatly simplifies the practical and cost effective integration of the present invention as a production tool. Small illumination areas result in the scattered light becoming very sensitive to particular features illuminated in a particular illumination area, with the changes in feature sizes not being averaged out. It is desirable to have a reasonable degree of spatial averaging on the wafer. Thus, the illumination area is preferably on the order of the average die size present on the wafer so the distribution of features within the illumination area does not change as the illumination area is moved over the wafer.

In addition, it is desirable to average in the scribe lines between the dies on the wafer, otherwise the process is sensitive to the exact placement of the illumination area. If the illumination area were required to be placed within a die area without encompassing any scribe lines, then the process would be limited to use only with dies of a certain size. Any smaller die in such a process would incorporate scribe lines in the measurement, and thus corrupt the measurement. Thus, the scribe lines are preferably averaged in using the present invention.

To accomplish this, about half of the illumination area is generally placed on a first die, while the other portion of the illumination area is placed on a second die. In this manner a scribe line is included in the measurement, which is a relatively small portion of the overall scatter signal recorded by the light detector. Using a large illumination area results in the ratio of the portion of the scatter signal that is scribe line, to the portion of the scatter signal that is actual circuit, remaining constant throughout the measuring process. Thus, the use of a large illumination area reduces the accuracy needed in positioning the illumination area relative to a die on the wafer, and therefore reduces or eliminates the need for image recognition systems for illumination positioning.

Next, in a gathering operation 406, a light detector gathers light scattered from the surface of the wafer. Preferably, the light is well collimated such that the scattered light rays traveling from one side of the illuminated area are parallel to the scattered rays traveling from the other side of the illuminated area. As with the light source, the light detector may detect the scattered light from the wafer surface directly, or indirectly using a mirror.

A decision is then made as to whether enough scatter data has been gathered to create a good scatter signature of the wafer, in a decision operation 408. If enough scatter data has been gathered to create a good scatter signature of the wafer, the method 400 continues with an analyzing operation 410. If enough scatter data has not been gathered to create a good scatter signature of the wafer, the method 400 continues with a step operation 412.

If enough scatter data has not been gathered to create good scatter signature of the wafer, the detector angle is stepped to the next detection angle, in a step operation 412. The light detector is preferably swept though a series of scatter angles to capture the scattered light data for creating the scatter signature of the wafer. Preferably, the detector is swept from about −70° to +70°. As described above, the light detector is preferably moved with a motor attached to a computer control system to provide an accurate correlation between the desired detection angle and the actual detection angle. After the detector angle is stepped, the method 400 continues with the gathering operation 406.

In an analysis operation 410, the gathered scatter data is analyzed. The scatter data is used by the present invention to create a scatter signature for the wafer. This scatter signature can be used for multiple purposes. First, the scatter signature may be used as an example of the scatter signature of a known good quality wafer. Preferably, the known good quality wafer is independently verified by another technique, such as SEM. Second, the scatter signature may be used to create quality bounds to create an envelope which bounds good quality wafer scatter signatures. Third, the scatter signature may be compared to the scatter signature of a good quality wafer to determine the quality of the current wafer. Preferably, this comparison is made using quality bounds created by statistical analysis of good quality wafers. If the scatter signature of the current wafer is within the quality bounds, the current wafer may be considered to be of good quality.

Finally, the analysis result may be used to assist in further processing of the wafer or dies, in operation 414. This further processing may include using the quality information to correct the etching process, or verify the process is performing as desired.

Figure 9:
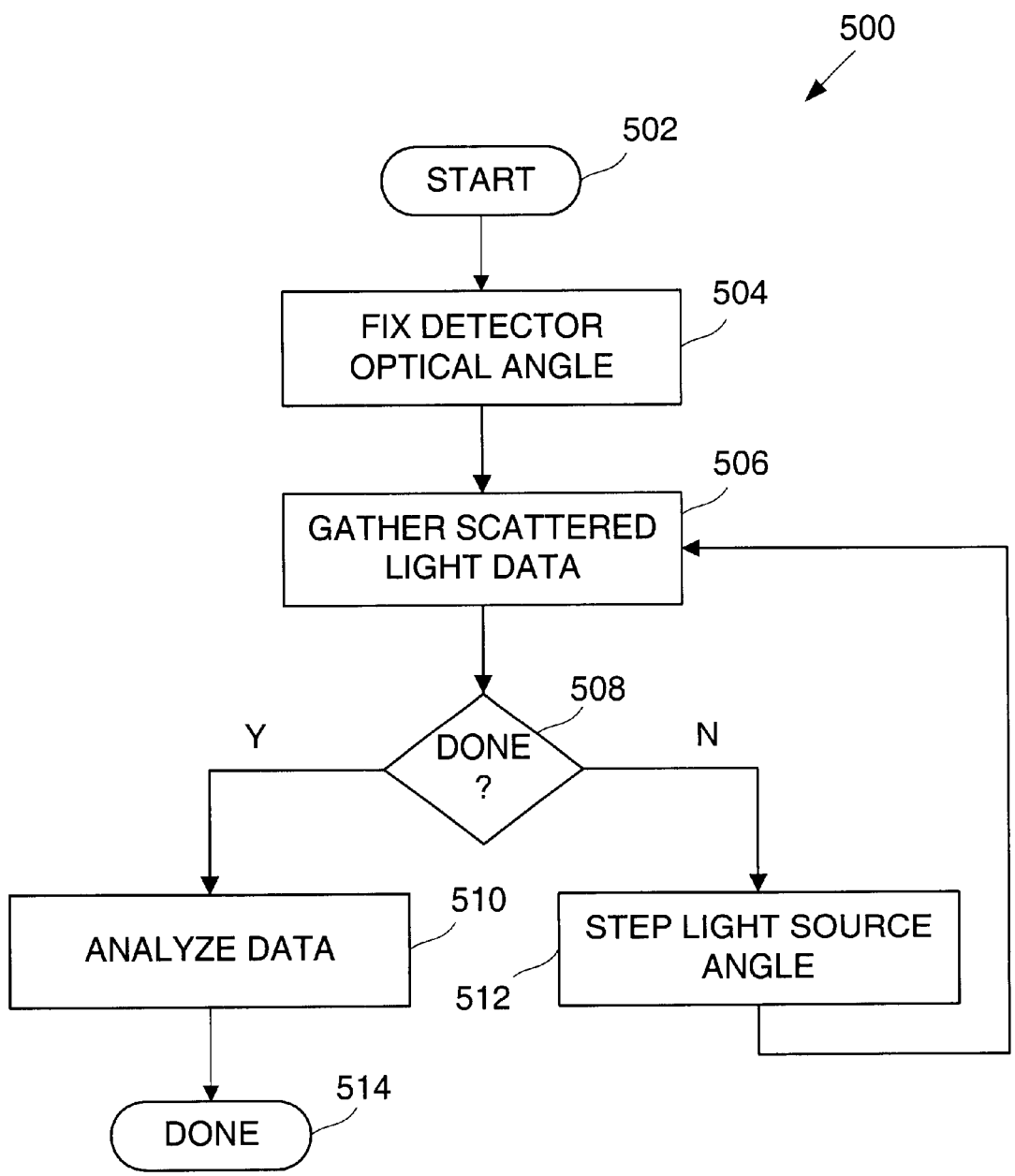
FIG. 9 is a flowchart showing a method for monitoring the feature characteristics of etched wafers, in accordance with another embodiment of the present invention.

FIG. 9 is a flowchart showing a method 500 for monitoring the feature characteristics of etched wafers, in accordance with another embodiment of the present invention. In an initial operation 502, preprocess operations are performed. Preprocess operations include preparing a wafer for etching, and etching the wafer.

In a fixed angle operation 504, a light detector optical angle is fixed. Preferably, detected light is well collimated such that the scattered light rays traveling from one side of the illuminated area are parallel to the scattered rays traveling from the other side of the illuminated area. As discussed above, the light detector may detect the scattered light from the wafer surface directly, or indirectly using a mirror.

Next, in a gathering operation 506, a well collimated light source illuminates the surface of the wafer and the light detector gathers the scattered light data. The collimated light source optical angle begins at a predetermined angle with the wafer surface. The light source is then used to illuminate an area on the surface of the wafer. As discussed above, the light source may directly illuminate the wafer surface, or indirectly illuminate the wafer surface using a mirror.

Preferably, the light is well collimated such that the scattered light rays traveling from one side of the illuminated area are parallel to the scattered rays traveling from the other side of the illuminated area. As with the light source, the light detector may detect the scattered light from the wafer surface directly, or indirectly using a mirror.

In addition, the light beam produced by light source is preferably spectrally broad. As described before, conventional scatterometery measures are generally performed using monochromatic light, typically from a laser. The present invention preferably uses a spectrally broadband light source to make the coherence length of the incident illumination short. In this manner, spatial information on the wafer, which corresponds to large-scale structures (such as details of the circuit pattern), is suppressed in the scatter signature.

Furthermore, the illumination area is preferably large to render the light intensity measurements insensitive to relative die position within the wafer. In addition, a large spot size greatly simplifies the practical and cost effective integration of the present invention as a production tool. Small illumination areas result in the scattered light becoming very sensitive to which particular features are illuminated in that particular illumination area, with changes in feature sizes not being averaged out. It is desirable to have a reasonable degree of spatial averaging on the wafer. Thus, the illumination area is preferably on the order of the average die size present on the wafer so the distribution of features within the illumination area does not change as the illumination area is moved over the wafer.

In addition, it is desirable to average in the scribe lines between the dies on the wafer, otherwise the process is sensitive to the exact placement of the illumination area. If the illumination area were required to be placed within a die area without encompassing any scribe lines, then the process would be limited to use only with dies of a certain size. Any smaller die in such a process would incorporate scribe lines in the measurement, and thus corrupt the measurement. Thus, the scribe lines are preferably averaged in using the present invention.

To accomplish this, about half of the illumination area is generally placed on a first die, while the other portion of the illumination area is placed on a second die. In this manner a scribe line is included in the measurement, which is a relatively small portion of the overall scatter signal recorded by the light detector. Using a large illumination area 1 results in the ratio of the portion of the scatter signal that is scribe line to the portion of the scatter signal that is actual circuit remaining constant throughout the measuring process. Thus, the use of a large illumination area reduces the accuracy needed in positioning the illumination area relative to a die on the wafer, and therefore reduces or eliminates the need for image recognition systems for illumination positioning.

A decision is then made as to whether enough scatter data has been gathered to create a good scatter signature of the wafer, in a decision operation 508. If enough scatter data has been gathered to create a good scatter signature of the wafer, the method 500 continues with an analyzing operation 510. If enough scatter data has not been gathered to create a good scatter signature of the wafer, the method 500 continues with a step operation 512.

If enough scatter data has not been gathered to create a good scatter signature of the wafer, the illumination incident angle is stepped to the next incident angle, in a step operation 512. The light source is preferably swept though a series of incident angles with a scattered light measurement made at each incident angle to create the scatter signature of the wafer. Preferably, the light source is swept from about 70° to near 0° (normal to the surface of the wafer). As described above, the light source is preferably moved with a motor attached to a computer control system to provide an accurate correlation between the desired illumination angle and the actual illumination angle. After the illumination angle is stepped, the method 500 continues with another gathering operation 506.

In an analysis operation 510, the gathered scatter data is analyzed. The scatter data is used by the present invention to create a scatter signature for the wafer. This scatter signature can be used for multiple purposes. First, the scatter signature may be used as an example of the scatter signature of a known good quality wafer. Preferably, the known good quality wafer is independently verified by another technique, such as SEM. Second, the scatter signature may be used to create quality bounds to create an envelope which bounds good quality wafer scatter signatures. Third, the scatter signature may be compared to the scatter signature of a good quality wafer to determine the quality of the current wafer. Preferably, this comparison is made using quality bounds created by statistical analysis of good quality wafers. If the scatter signature of the current wafer is within the quality bounds, the current wafer may be considered to be of good quality.

Finally, the analysis result may be used to assist in further processing of the wafer or dies, in operation 514. This further processing may include using the quality information to correct the etching process, or verify that the process is performing as desired.

Figure 10:
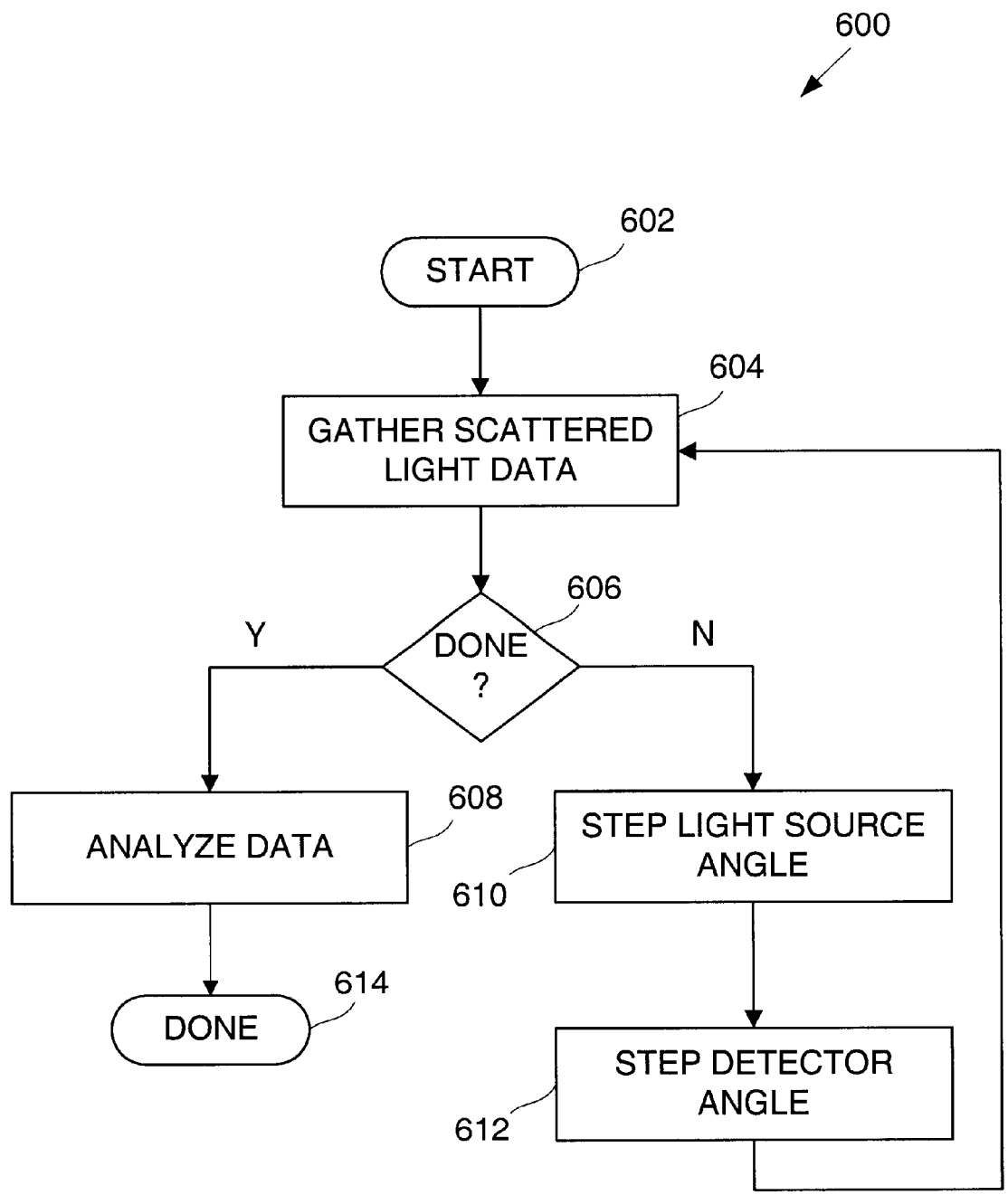
FIG. 10 is a flowchart showing a method for monitoring the feature characteristics of etched wafers, in accordance with an embodiment of the present invention.

FIG. 10 is a flowchart showing a method 600 for monitoring the feature characteristics of etched wafers, in accordance with an embodiment of the present invention. In an initial operation 602, preprocess operation are performed. Preprocess operations include preparing a wafer for etching, and etching the wafer. In addition, initial predetermined angles are set for a collimated light source and a light detector. As discussed above, the light source and light detector may directly illuminate and gather data from the wafer surface, or do so indirectly using a mirror.

The light beam produced by the light source is preferably spectrally broad. As described before, conventional scatterometry measures are generally performed using monochromatic light, typically from a laser. The present invention preferably uses a spectrally broadband light source to make the coherence length of the incident illumination short. In this manner, spatial information on the wafer, which corresponds to large-scale structures (such as details of the circuit pattern), is suppressed in the scatter signature.

Furthermore, the illumination area is preferably large to render the light intensity measurements insensitive to relative die position within the wafer. In addition, a large spot size greatly simplifies the practical and cost effective integration of the present invention as a production tool. Small illumination areas result in the scattered light becoming very sensitive to which particular features are illuminated in that particular illumination area, with changes in feature sizes not being averaged out. It is desirable to have a reasonable degree of spatial averaging on the wafer. Thus, the illumination area is preferably on the order of the average die size present on the wafer so the distribution of features within the illumination area does not change as the illumination area is moved over the wafer.

In addition, it is desirable to average in the scribe lines between the dies on the wafer, otherwise the process is sensitive to the exact placement of the illumination area. If the illumination area were required to be placed within a die area without encompassing any scribe lines, then the process would be limited to use only with dies of a certain size. Any smaller die in such a process would incorporate scribe lines in the measurement, and thus corrupt the measurement. Thus, the scribe lines are preferably averaged in using the present invention.

To accomplish this, about half of the illumination area is generally placed on a first die, while the other portion of the illumination area is placed on a second die. In this manner a scribe line is included in the measurement, which is a relatively small portion of the overall scatter signal recorded by the light detector. Using a large illumination area results in the ratio of the portion of the scatter signal that is scribe line, to the portion of the scatter signal that is actual circuit, remaining constant throughout the measuring process. Thus, the use of a large illumination area reduces the accuracy needed in positioning the illumination area relative to a die on the wafer, and therefore reduces or eliminates the need for image recognition systems for illumination positioning.

In a gathering operation 604, the light source illuminates an area on the surface of the wafer and the light detector gathers light scattered from the illuminated area. Preferably, the light is well collimated such that the scattered light rays traveling from one side of the illuminated area are parallel to the scattered rays traveling from the other side of the illuminated area.

A decision is then made as to whether enough scatter data has been gathered to create a good scatter signature of the wafer, in a decision operation 606. If enough scatter data has been gathered to create a good scatter signature of the wafer, the method 600 continues with an analyzing operation 608. If enough scatter data has not been gathered to create a good scatter signature of the wafer, the method 600 continues with a step source operation 610.

If enough scatter data has not been gathered to create a good scatter signature of the wafer, the illumination incident angle is stepped to the next incident angle, in a step source operation 610. The light source is preferably swept though a series of incident angles with a scattered light measurement made at each incident angle to create the scatter signature of the wafer. Preferably, the light source is swept from about 0° normal to the surface to 70°. As described above, the light source is preferably moved with a motor attached to a computer control system to provide an accurate correlation between the desired illumination angle and the actual illumination angle.

Next, in a step detector operation 612, the detector angle is stepped to the next detection angle. The light detector is preferably swept though a series of scatter angles to capture the scattered light data for creating the scatter signature of the wafer. Preferably, the detector is swept from about −70° to +70°. The offset angle between the light source and the light detector may be varied to create the wafer scatter signature. As with the light source, the light detector is preferably moved with a motor attached to a computer control system to provide an accurate correlation between the desired detection angle and the actual detection angle. After the detector angle is stepped, the method 600 continues with another gathering operation 604.

In an analysis operation 608, the gathered scatter data is analyzed. The scatter data is used by the present invention to create a scatter signature for the wafer. This scatter signature can be used for multiple purposes. First, the scatter signature may be used as an example of the scatter signature of a known good quality wafer. Preferably, the known good quality wafer is independently verified by another technique, such as SEM. Second, the scatter signature may be used to create quality bounds to create an envelope which bounds good quality wafer scatter signatures. Third, the scatter signature may be compared to the scatter signature of a good quality wafer to determine the quality of the current wafer. Preferably, this comparison is made using quality bounds created by statistical analysis of good quality wafers. If the scatter signature of the current wafer is within the quality bounds, the current wafer may be considered to be of good quality.

Finally, the analysis result may be used to assist in further processing of the wafer or dies, in operation 614. This further processing may include using the quality information to correct the etching process, or verify the process is performing as desired.

Figure 11:
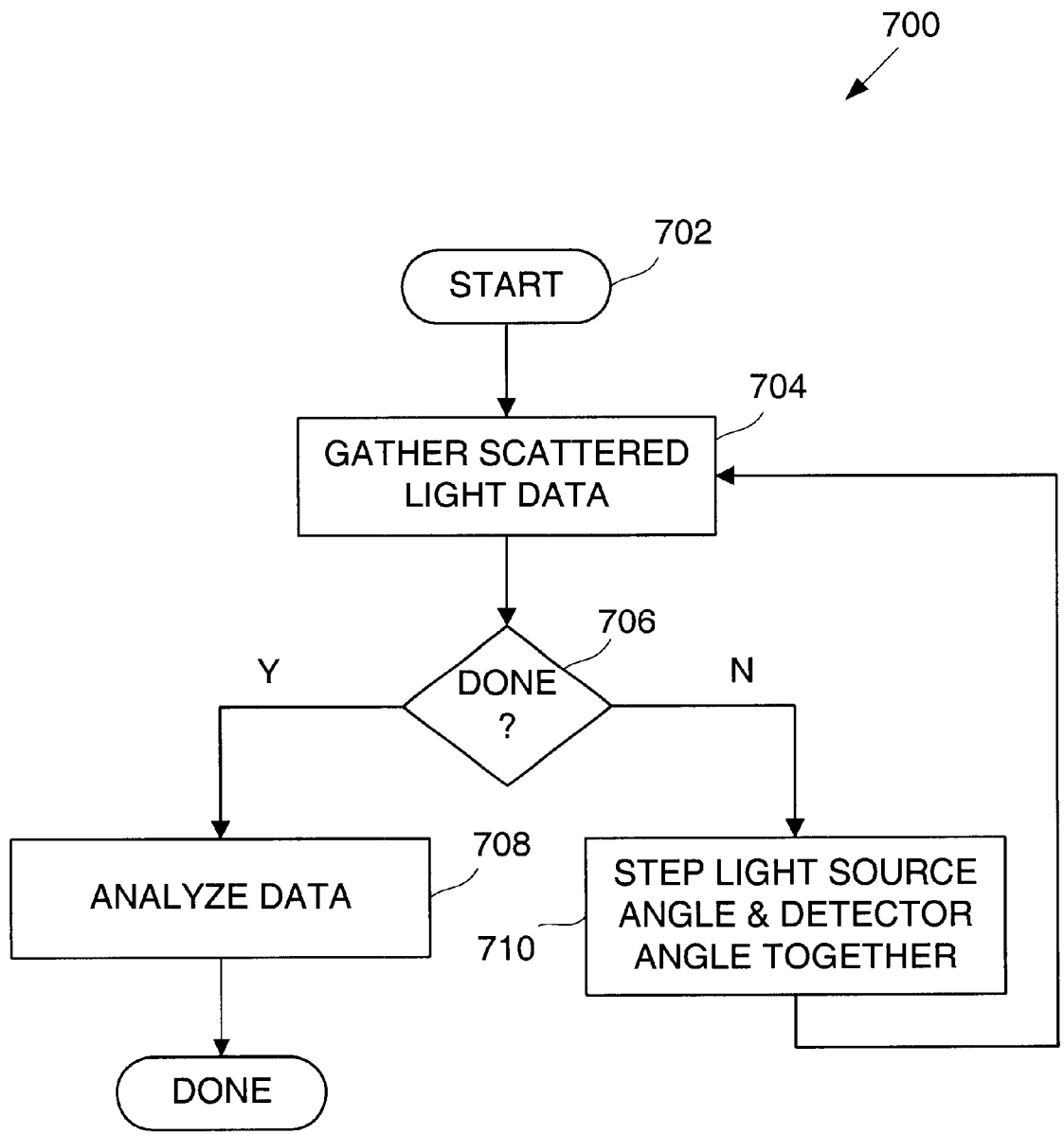
FIG. 11 is a flowchart showing a method for monitoring the feature characteristics of etched wafers, in accordance with an embodiment of the present invention.

FIG. 11 is a flowchart showing a method 700 for monitoring the feature characteristics of etched wafers, in accordance with an embodiment of the present invention. In an initial operation 702, preprocess operation are performed. Preprocess operations include preparing a wafer for etching, and etching the wafer. Furthermore, initial a predetermined angle is set for a collimated light source and a light detector. Preferably, the collimated light source and light detector are set at a fixed offset angle from each other. In addition, the offset angle is preferably set at 0° in order to use the same optics for both the light source and light detector. As discussed above, the light source and light detector may directly illuminate and gather data from the wafer surface, or do so indirectly using a mirror.

The light beam produced by light source is preferably spectrally broad. As described before, conventional scatterometry measures are generally performed using monochromatic light, typically from a laser. The present invention preferably uses a spectrally broadband light source to make the coherence length of the incident illumination short. In this manner, spatial information on the wafer, which corresponds to large-scale structures (such as details of the circuit pattern), is suppressed in the scatter signature.

Furthermore, the illumination area is preferably large to render the light intensity measurements insensitive to relative die position within the wafer. In addition, a large spot size greatly simplifies the practical and cost effective integration of the present invention as a production tool. Small illumination areas result in the scattered light becoming very sensitive to which particular features are illuminated in that particular illumination area, with changes in feature sizes not being averaged out. It is desirable to have a reasonable degree of spatial averaging on the wafer. Thus, the illumination area is preferably on the order of the average die size present on the wafer so the distribution of features within the illumination area does not change as the illumination area is moved over the wafer.

In addition, it is desirable to average in the scribe lines between the dies on the wafer, otherwise the process is sensitive to the exact placement of the illumination area. If the illumination area were required to be placed within a die area without encompassing any scribe lines, then the process would be limited to use only with dies of a certain size. Any smaller die in such a process would incorporate scribe lines in the measurement, and thus corrupt the measurement. Thus, the scribe lines are preferably averaged in using the present invention.

To accomplish this, about half of the illumination area is generally placed on a first die, while the other portion of the illumination area is placed on a second die. In this manner a scribe line is included in the measurement, which is a relatively small portion of the overall scatter signal recorded by the light detector. Using a large illumination area results in the ratio of the portion of the scatter signal that is scribe line, to the portion of the scatter signal that is actual circuit, remaining constant throughout the measuring process. Thus, the use of a large illumination area reduces the accuracy needed in positioning the illumination area relative to a die on the wafer, and therefore reduces or eliminates the need for image recognition systems for illumination positioning.

In a gathering operation 704, the light source illuminates and area the surface of the wafer and the light detector gathers light scattered from the illuminated area. Preferably, the light is well collimated such that the scattered light rays traveling from one side of the illuminated area are parallel to the scattered rays traveling from the other side of the illuminated area.

A decision is then made as to whether enough scatter data has been gathered to create a good scatter signature of the wafer, in a decision operation 706. If enough scatter data has been gathered to create a good scatter signature of the wafer, the method 700 continues with an analyzing operation 708. If enough scatter data has not been gathered to create a good scatter signature of the wafer, the method 700 continues with a step source operation 710.

If enough scatter data has not been gathered to create a good scatter signature of the wafer, the illumination incident angle and the detection angle are stepped to the next angle, in a step source operation 710. It should be borne in mind that the offset angle between the light source and the light detector remains constant in method 700.

Moreover, the light source and light detector are preferably swept though a series of angles with a scattered light measurement made at each incident angle to create the scatter signature of the wafer. Preferably, the light source and light detector are swept from about −70° to +70°. As described above, the light source and light detector are preferably moved with motors attached to a computer control system to provide an accurate correlation between the desired illumination and detection angles and the actual angle. After the detector angle is stepped, the method 700 continues with another gathering operation 704.

In an analysis operation 708, the gathered scatter data is analyzed. The scatter data is used by the present invention to create a scatter signature for the wafer. This scatter signature can be used for multiple purposes. First, the scatter signature may be used as an example of the scatter signature of a known good quality wafer. Preferably, the known good quality wafer is independently verified by another technique, such as SEM. Second, the scatter signature may be used to create quality bounds to create an envelope, which bounds good quality wafer scatter signatures. Third, the scatter signature may be compared to the scatter signature of a good quality wafer to determine the quality of the current wafer. Preferably, this comparison is made using quality bounds created by statistical analysis of good quality wafers. If the scatter signature of the current wafer is within the quality bounds, the current wafer may be considered to be of good quality.

Finally, the analysis result may be used to assist in further processing of the wafer or dies, in operation 614. This further processing may include using the quality information to correct the etching process, or verify the process is performing as desired.

While the present invention has been described in terms of several preferred embodiments, there are many alterations, permutations, and equivalents which may fall within the scope of this invention. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A method for monitoring feature characteristics of etched wafers, comprising the operations of:

illuminating an area of a first wafer utilizing one light beam from a highly collimated light source, wherein the one light beam from the light source is broadband multi-spectral light, wherein the entire one beam illuminates the area from one angle to a surface of the wafer at any one time and the one beam is scattered from the illuminated area, wherein the one angle of the light beam illuminating the illuminated area is varied at different times in the range of about normal to the surface of the wafer to about seventy degrees to the surface;

measuring an angular distribution of the light scattered from the illuminated area of the first wafer, the measurement of the distribution being gathered at variable angles, each of the variable angles having a fixed angle of offset from a respective one of the varied angles of the one light beam illuminating the illuminated area; and comparing a scatter signature of the first wafer obtained from the measuring of the one beam with a known scatter signature of a second wafer in order to determine a quality of the first wafer.

2. A method for monitoring feature characteristics of etched wafers, comprising the operations of:

illuminating an area of a first wafer utilizing a highly collimated light source, wherein light from the light source that is incident on the illuminated area is broadband multi-spectral light that is scattered from the illuminated area to form scattered light at various scattering angles, the size of the illuminated area being no less than 50% of a repeating unit size of a feature characteristic of the wafer;

measuring the intensity of the light scattered from the illuminated area of the first wafer; and comparing a scatter signature of the first wafer with a known scatter signature of a second wafer.

3. A method as recited in claim 2, wherein the illuminating operation causes the size of the illuminated area to be no less than the size of the repeating unit of the feature characteristic of the wafer.

4. A method as recited in claim 3, wherein a feature characteristic of the wafer also includes a second feature characteristic between the adjacent repeating units, and wherein:

the illuminating operation causes the illuminated area to illuminate approximately one-half of a first repeating unit of the feature characteristic and to illuminate approximately one-half of a second repeating unit of the feature characteristic, and wherein the illuminated area includes the second feature characteristic between the first and second repeating units.

5. A method of monitoring feature characteristics of etched wafers, the feature characteristics including a plurality of die on the surface of the wafer, the die having an average size, the method comprising the operations of:

illuminating an area of a first wafer utilizing a highly collimated light source, wherein the size of the illuminated area has a value approximately equal to the average die size, wherein light from the light source that is incident on the illuminated area is broadband multi-spectral light that is scattered from the illuminated area to form scattered light;

measuring the intensity of the light scattered from the illuminated area of the first wafer; and comparing a scatter signature of the first wafer with a known scatter signature of a second wafer.

6. A method as recited in claim 5, wherein:

the illuminating operation causes the illuminated area to illuminate approximately one-half of a first one of the die and to illuminate approximately one-half of a second one of the die, and wherein the first and second die are adjacent die.

7. A method as recited in claim 6, wherein the feature characteristic of the wafer also includes a non-die feature between the first and second die, and wherein:

the illuminating operation causes the illuminated area to also illuminate the non-die feature between the first and second die.

* * * * *